US00PP11037P

United States Patent [19]

Yomo et al.

[11] Patent Number: Plant 11,037

[45] Date of Patent: Aug. 24, 1999

[54] VERBENA PLANT NAMED 'SUNMARIRIPI'

[75] Inventors: Yasunori Yomo, Yamanashi; Yasuyuki Murakami, Shiga, both of Japan

[73] Assignee: Suntory Limited, Osaka, Japan

[21] Appl. No.: 08/923,777

[22] Filed: Sep. 4, 1997

[30] Foreign Application Priority Data

Sep. 4, 1996 [JP] Japan ..... 9059

[51] Int. Cl.[6] ..... A01H 5/00

[52] U.S. Cl. ..... Plt./308

[58] Field of Search ..... Plt./87, 308

[56] References Cited

U.S. PATENT DOCUMENTS

| | | | |
|---|---|---|---|
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,411 | 12/1995 | Tachibana et al. | Plt./87 |

OTHER PUBLICATIONS

GTITM UPOVROM Citation for 'Sanmariripi' as per JP PBR 9059, Sep. 4, 1996.

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

Disclosed herein is a verbena plant which has a broad spreading growth habit and long stems. The plant forms flowers in clusters with a great profusion of blooms. The blooming period is late April to November and flowering duration is long. The entire plant remains in bloom for a considerable period of time. The flower size is large and the petal color of flowers is purplish pink. The plant is highly tolerant to heat, and exhibits a high resistance to pests and diseases, particularly powdery mildew, and a high resistance to rain.

2 Drawing Sheets

BACKGROUND OF THE VARIETY

The present invention relates to a new and distinct variety of *Verbena hybrida* plant obtained from crossing a *Verbena hybrida* plant named 'Novaris Rosepink with eye' (♀) and a wild type of verbena plant, *Verbena peruviana* (♂), native to Brazil.

The verbena is a very popular plant and is used for flower bedding and potting in the summer season. There are only a few varieties of the verbena plant which have a spreading growth habit, much branching, a large number of flowers in a cluster and which have a high resistance to rain, heat, cold, and diseases. Accordingly, this invention was aimed at obtaining a new variety having a spreading growth habit, strong branching, a large number of flowers in a cluster, a flower of large diameter, a high tolerance to heat and cold, resistance to diseases and pests, and also having purplish pink colored petals.

The new variety of verbena plant according to this invention originated from the crossing of a *Verbena hybrida* plant named 'NOVARIS Rosepink with eye' (non-patented in the United States) (♀) and a wild type of verbena plant, *Verbena peruviana* (♂), native to Brazil.

Initially, 50 seedlings were obtained in the autumn of 1994, from crossing 'NOVARIS Rosepink with eye' as female parent and a wild type of verbena plant (*Verbena peruviana f. rosea*) as pollen parent in May of 1994. From this crossing, 3 seedlings were selected in view of spreading growth habit and were propagated by cuttings, and then grown as a trial by flower bedding and planters from the spring of 1995. Finally, only one plant was selected from these 3 seedlings in the autumn of 1995 and the botanical characteristics of the seedling were examined, using the similar varieties 'Sumaripi' (non-patented in the United States) and 'NOVARIS Rosepink with eye' for comparison. As a result, it was concluded that this *Verbena hybrida* plant is distinguishable from any other variety, whose existence is known to us, and is uniform and stable in its characteristics. The new variety of verbena plant of the present invention was named 'Sunmariripi'.

In the following description, the color-coding is in accordance with The Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Colour Chart) is also added for reference.

'NOVARIS Rosepink with eye' was used as the female parent when obtaining this new variety, 'Sunmariripi', and is publically available. The main botanical characteristics of 'NOVARIS Rosepink with eye' when grown at the Hakushu Nursery Center of SUNTORY ltd., 2913-1 Torihara, Hakushu-cho, Kitakoma-gun, Yamanashi-ken, Japan are as follows.

Plant:
- *Growth habit.*—Erect.
- *Plant height.*—20–30 cm.
- *Plant extension.*—15–20 cm.

Stem:
- *Diameter.*—2.0–3.0 mm.
- *Anthocyanin pigmentation.*—Absent.
- *Branching.*—Medium.
- *Pubescence.*—Medium.
- *Length of internode.*—3.0–4.0 cm.

Leaf:
- *Phyllotaxis.*—Opposite.
- *Shape of blade.*—Hastate.
- *Length.*—3.0–4.0 cm.
- *Width.*—2.0–2.5 cm.
- *Depth of incision.*—Shallow.
- *Color.*—Dark yellow green (R.H.S. 146A, JHS 3508).
- *Pubescence.*—Few.

Flower:
*Facing direction*.—Upward.
*Outward curvature of petal*.—Slightly curved.
*Diameter*.—1.5–2.0 cm.
*Height*.—20–30 mm.
*Color*.—Deep pink (R.H.S. 52C, JHS 0105).
*Color intensity*.—Absent. .
*Overlapping of petals*.—Opened.
*Flower cluster*.—30–40 mm in length; and 40–50 mm in diameter.
*Calyx*.—1.0–1.5 cm in length.
*Anthocyanin pigmentation of calyx limb*.—Absent.
*Peduncle*.—2–3 mm in thickness; and 50–60 cm in length.
*Number of flowers*.—Medium (approximately 10–14).
*Reproductive organs*.—1 pistil and 4 stamens.
*Flower fragrance*.—Absent.
*Flowering duration*.—Long.
Physiological and ecological characteristics: Low resistance to diseases and pests, and low tolerance to heat and cold.

The pollen parent used when obtaining the new variety, 'Sunmariripi', was a wild type of verbena native to South Brazil and botanically known as *Verbena peruviana*. This wild type of verbena plant is presently maintained at the Hakushu Nursery Center of SUNTORY Ltd., residing at 2913-1 Torihara, Hakushu-cho, Kitakoma-gun, Yamanashi-ken, Japan. The main botanical characteristics of this pollen parent are as follows when grown at this location.

Plant:
*Growth habit*.—Spreading.
*Plant height*.—10–20 cm.
*Plant extension*.—100–150 cm.
Stem:
*Diameter*.—1.0–2.0 mm.
*Anthocyanin pigmentation*.—Present.
*Branching*.—Medium.
*Pubescence*.—Medium.
*Length of internode*.—3.0–4.0 cm.
Leaf:
*Phyllotaxis*.—Opposite.
*Shape of blade*.—Hastate.
*Length*.—3.0–4.0 cm.
*Width*.—1.5–2.0 cm.
*Depth of incision*.—Shallow.
*Color*.—Medium olive green (R.H.S. 146A, JHS 3509).
*Pubescence*.—Few.
Flower:
*Facing direction*.—Upward.
*Outward curvature of petal*.—Slightly curved.
*Diameter*.—2.0–3.0 cm.
*Height*.—20–30 mm.
*Color*.—Strong reddish purple (R.H.S. 77B, JHS 8911).
*Color intensity*.—Absent.
*Overlapping of petals*.—Opened.
*Flower cluster*.—30–40 mm in length; and 50–60 mm in diameter.
*Calyx*.—1.5–2.0 cm in length.
*Anthocyanin pigmentation of calyx limb*.—Absent.
*Peduncle*.—1–2 mm in thickness; and 3.0–5.0 cm in length.
*Number of flowers*.—Plentiful (approximately 10–14).
*Reproductive organs*.—1 pistil and 4 stamens.
*Flower fragrance*.—Absent.
*Flowering duration*.—Short.
Physiological and ecological characteristics: High resistance to diseases and pests, and high tolerance to heat and cold.

'Sunmaripi' was used as a comparison for this new variety 'Sunmariripi'. The main botanical characteristics of 'Sunmaripi' are as follows when grown at the Hakushu Nursery Center of SUNTORY Ltd., 2913-1 Torihara, Hakushu-cho, Kitakoma-gun, Yamanashi-ken, Japan.

Plant:
*Growth habit*.—Spreading.
*Plant height*.—15–25 cm.
*Plant extension*.—50–70 cm.
*Growth*.—Very vigorous with abundant branching and great profusion of blooms with the whole plant remaining in bloom for a considerable period of time.
Stem:
*Diameter*.—2.0–3.0 mm.
*Anthocyanin pigmentation*.—Present.
*Branching*.—Abundant.
*Pubescence*.—Medium.
*Length of internode*.—4.0–5.0 cm.
Leaf:
*Phyllotaxis*.—Opposite.
*Shape of blade*.—Hastate.
*Length*.—4.0–5.0 cm.
*Width*.—2.0–2.5 cm.
*Depth of incision*.—Shallow.
*Color*.—Grayish olive green (R.H.S. 137A-137B, JHS 3716).
*Pubescence*.—Few.
Flower:
*Facing direction*.—Upward.
*Outward curvature of petal*.—Curved.
*Diameter*.—1.5–2.0 cm.
*Height*.—20 mm.
*Color*.—Deep purplish pink (R.H.S. 70C, JHS 9213).
*Color intensity*.—Present.
*Overlapping of petals*.—Separate.
*Flower cluster*.—30–35 mm in length; and 50–55 mm in diameter.
*Calyx*.—1.0 cm in length.
*Anthocyanin pigmentation of calyx limb*.—Present.
Peduncle.—2–3 mm in thickness; and 5.0–6.0 cm in length.
*Number of flowers*.—Plentiful (approximately 13–15).
*Reproductive organs*.—1 pistil and 5 stamens.
*Flower fragrance*.—Absent.
*Flowering duration*.—Long.
Physiological and ecological characteristics: High resistance to diseases and pests, particularly powdery mildew. High tolerance to heat and moderate tolerance to cold.

This new variety of verbena plant, 'Sunmariripi', was asexually reproduced by cuttings at the aforementioned Hakushu Nursery Center of SUNTORY Ltd., at 2913-1 Torihara, Hakushu-cho, Kitakoma-gun, Yamanashi-ken, Japan, and the homogeneity and stability thereof were confirmed. The characteristics of the new variety are fully stable following such asexual reproduction.

SUMMARY OF THE VARIETY

This new variety of verbena plant has a broad spreading growth habit and long stems. The plant is well branched and abundantly forms flowers in a cluster. The blooms are present in profusion. The blooming period is late April to November and flowering duration is long. The entire plant remains in bloom for an extended period of time. The flower size is large and the petal coloration of the flowers is purplish pink. The plant is highly tolerant to heat, exhibits a high resistance to pests and diseases, particularly powdery mildew, and a high resistance to rain. Medium resistance to cold is exhibited.

DESCRIPTION OF THE VARIETY

Figure 1:
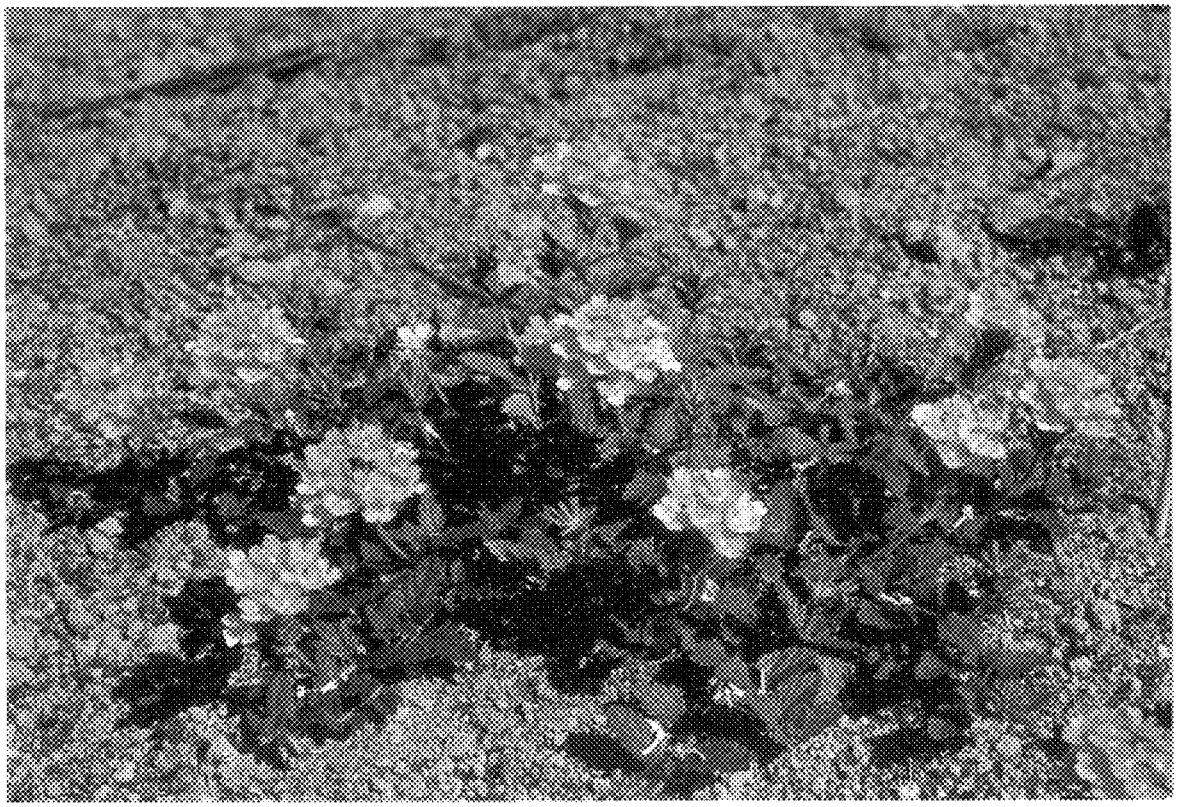
FIG. 1 depicts a side view of the 'Sunmariripi' plant of the present invention.
Figure 2:
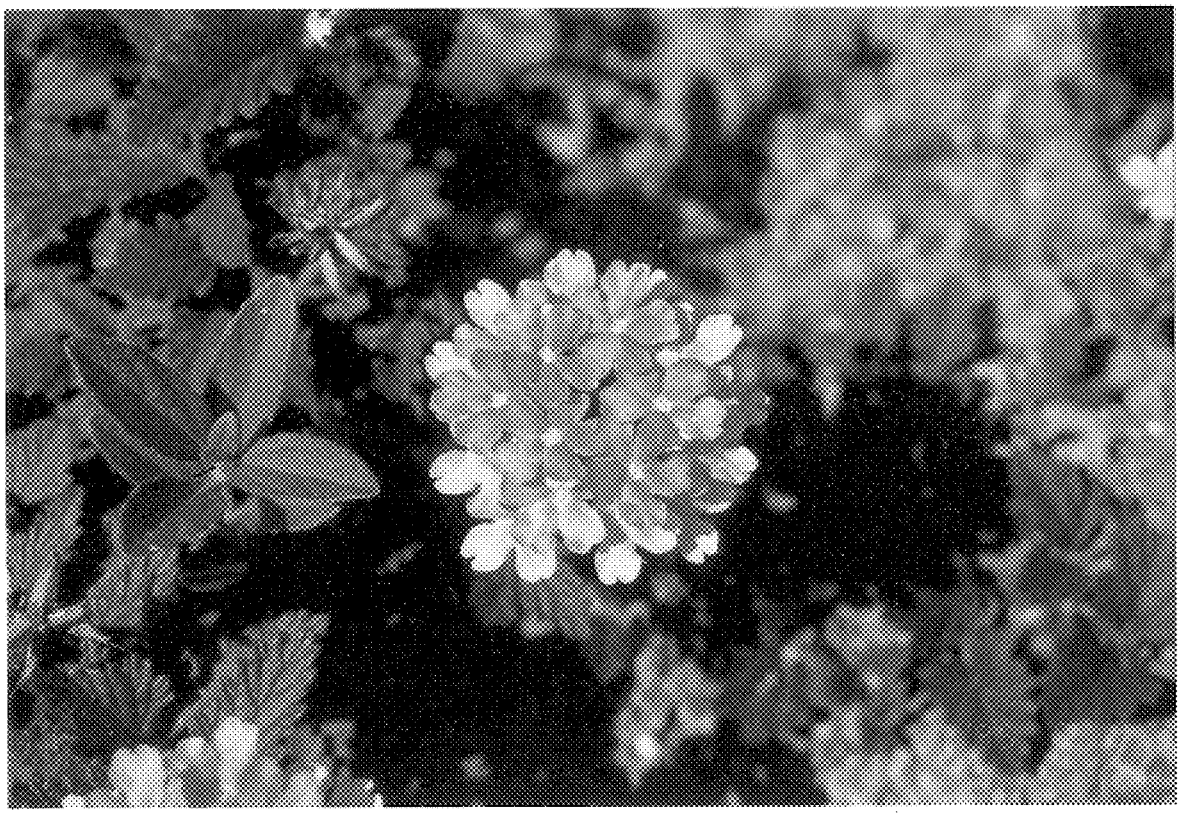
FIG. 2 depicts a close-up view of the flowers of the 'Sunmariripi' plant of the present invention.

The botanical characteristics of the new and distinct variety of verbena plant, 'Sunmariripi' are as follows when grown at the Hakushu Nursery Center of SUNTORY Ltd., 2913-1 Torihara, Hakushu-cho, Kitakoma-gun, Yamanashi-ken, Japan.

Plant:
- *Growth habit.*—Spreading.
- *Plant width.*—Broad; 50–70 cm.
- *Plant height.*—Medium; 10–20 cm.

Stem:
- *Diameter.*—Medium; 2.0–3.0 mm.
- *Anthocyanin pigmentation.*—Present.
- *Pubescence.*—Medium.
- *Branching.*—A moderate level of branching is present. Each single branch commonly produces two additional branches. More specifically, a single branch commonly becomes three branches and those three branches commonly produce nine branches, etc.
- *Subterranean stem.*—Absent. But when the stems contact the surface of soil, the nodes take root in the ground and the plant growth thereby spreads.
- *Length of internode.*—Medium; 2.0–4.0 cm.
- *Color.*—R.H.S. 144A, JHS 3507.

Leaf:
- *Phyllotaxis.*—Opposite.
- *Shape of blade.*—Ovate.
- *Depth of blade incision.*—Shallow.
- *Blade margin.*—Serrate.
- *Length.*—Medium.
- *Width.*—Medium.
- *Leaf apex.*—Mucronate.
- *Leaf base.*—Petiolate.
- *Color.*—Grayish olive green (R.H.S. 137A, JHS 3716) on the upper surface and moderate yellow green (R.H.S. 144A and JHS 3513 on the under surface).
- *Pubescence.*—Few.
- *Petiole.*—Present.
- *Petiole color.*—R.H.S. 144A, JHS 3507.
- *Diameter of petiole.*—Medium.
- *Length of petiole.*—Short; 2.0–2.2 mm.

Flower:
- *Shape of cluster.*—Obovate.
- *Length of cluster.*—Medium; 30–61 mm.
- *Diameter of cluster.*—Medium; 51–56 mm.
- *Facing direction.*—Upward.
- *Outward curvature of petal.*—Slightly curved.
- *Diameter.*—Large; 1.5–2.0 cm.
- *Height.*—Medium.
- *Color.*—Purplish pink (R.H.S. 55A, JHS 9705) on the upper surface and light purplish pink (R.H.S. 65B, JHS 9203) on the under surface. The petal coloration fades slightly with age.
- *Eye color.*—R.H.S. 11D, JHS 2503.
- *Eye size.*—Small.
- *Variegation on petal.*—Absent.
- *Color presentation.*—Substantially even.
- *Color intensity.*—Absent.
- *Overlapping of petals.*—Separate.
- *Incision of petal.*—Present.
- *Number of petals.*—Medium; 5.
- *Sepal.*—Tubular in configuration.
- *Length of calyx.*—Long.
- *Anthocyanin pigmentation of calyx limb.*—Absent.
- *Shape of pistil.*—Two lobes.
- *Color of anther.*—Yellow green.
- *Diameter of peduncle.*—Thin; 1–2 mm.
- *Color of peduncle.*—Strong yellow green, R.H.S. 144A, JHS 3507.
- *Length of peduncle.*—Medium; 28–32 mm.
- *Number of flowers.*—Plentiful; commonly 20±2.
- *Flower bearing.*—In a cluster (as illustrated).
- *Reproductive organs.*—1 pistil and 4 stamens.
- *Pollen.*—Brilliant greenish-yellow (R.H.S. 6C, JHS 2704) in coloration.
- *Flower fragrance.*—Absent.
- *Flowering time.*—Early.
- *Flowering duration.*—Long. When planted during March, the plant commonly blossoms from April to November. A bloom cluster commonly is present for approximately 2 to 3 weeks, and an individual bloom within the cluster commonly lasts for approximately 7 to 10 days on the plant. ly powdery mildew. High tolerance to heat, cold and drought. High tolerance to rain. Medium tolerance to cold.

This new variety of verbena plant is most suitable for flower bedding and potting, particularly in planters, and is further excellent for use as a ground cover.

The plant of this new variety, 'Sunmariripi', is presently planted and maintained at the Hakushu Nursery Center of SUNTORY Ltd., 2913-1 Torihara, Hakushu-cho, Kitakoma-gun, Yamanashi-ken, Japan.

We claim:

1. A new and distinct variety of *Verbena hydrida* plant having the following combination of characteristics:

(a) exhibits a spreading growth habit with long stems,
(b) forms in abundance clusters of attractive purplish pink blossoms that remain on the plant for an extended period of time, and
(c) exhibits good tolerance to rain, heat, drought, and diseases;

substantially as shown and described.

* * * * *